United States Patent [19]

Miller

[11] 4,416,039

[45] Nov. 22, 1983

[54] ARTERY OR VEIN PERFORATOR

[76] Inventor: Judith A. Miller, P.O. Box 5068, Pine Bluff, Ark. 71611

[21] Appl. No.: 277,911

[22] Filed: Jun. 26, 1981

[51] Int. Cl.³ .............................................. A01N 1/00
[52] U.S. Cl. ............................................ 27/21; 30/363
[58] Field of Search ............... 27/21, 1; 128/305, 329, 128/310; 30/358, 363, 364, 366, 92

[56] References Cited

U.S. PATENT DOCUMENTS 2,145,210   1/1939   Chason ................................. 30/363

FOREIGN PATENT DOCUMENTS 963076   1/1955   Fed. Rep. of Germany .......... 30/92
470632   6/1914   France ................................... 30/363
503533   6/1920   France ................................... 30/363

Primary Examiner—John D. Yasko
Attorney, Agent, or Firm—Stephen D. Carver

[57] ABSTRACT

Apparatus for manually perforating blood vessels preparatory to embalming. The apparatus preferably comprises a pair of handle members adapted to be squeezed together to close a jaw whereby to penetrate the artery or vein with an appropriate needle. In the preferred embodiment pivotal fork means are included to help manipulate the vein or artery to be perforated. The vein or artery may be properly aligned with a channel member formed in one of the jaws. Notch means are preferably formed in the fork to assist in alignment of the blood vessel to be punctured.

24 Claims, 9 Drawing Figures

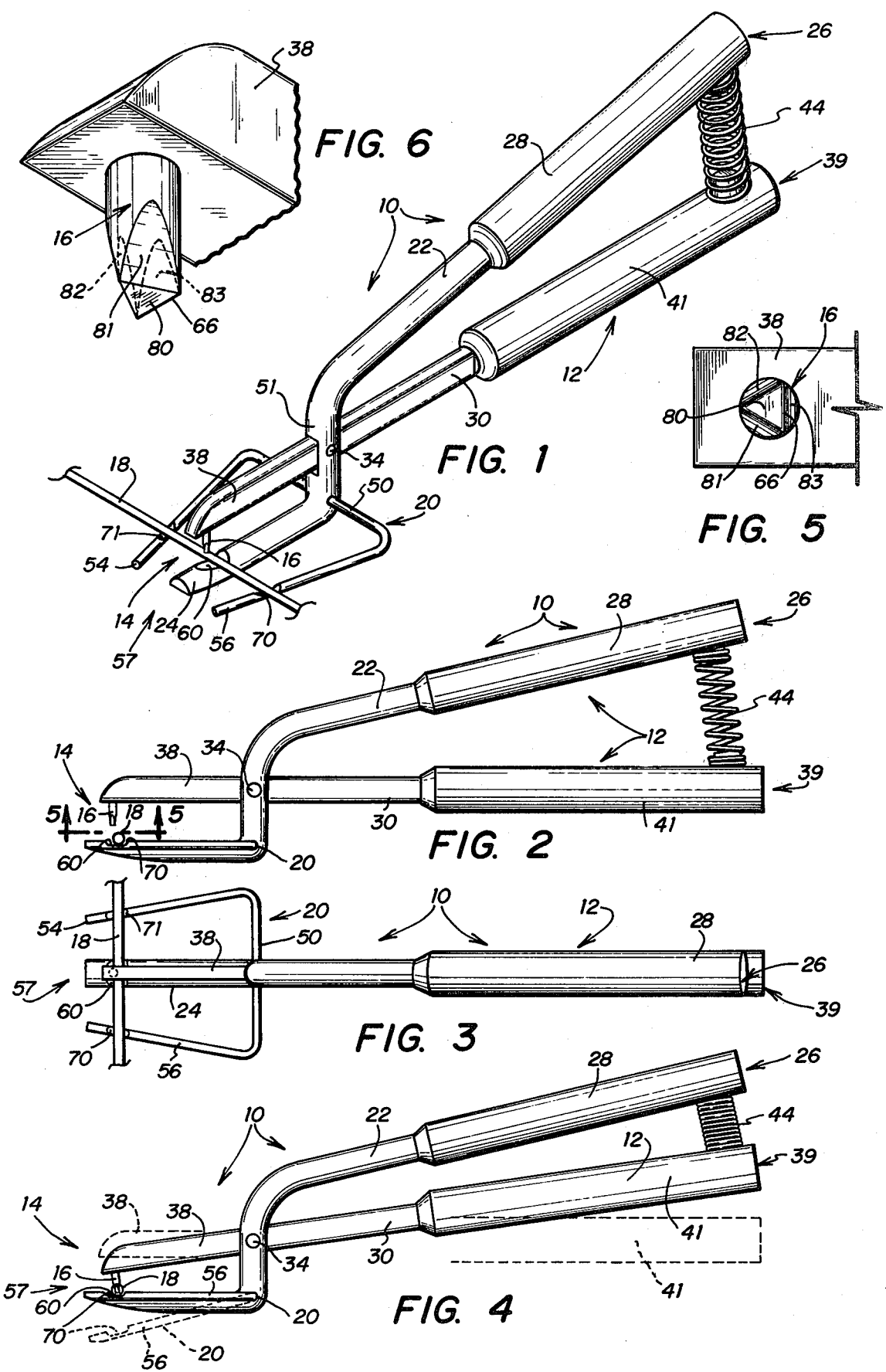

ARTERY OR VEIN PERFORATOR

BACKGROUND OF THE INVENTION

The present invention relates generally to surgical devices. More particularly, the present invention is directed to apparatus ideally adapted for use by morticians to puncture the vein or artery of the deceased prior to interconnection with a conventional embalming machine.

Prior to embalming of the deceased the mortician must decide upon the proper vein and artery for subsequent connection to the embalming apparatus. As blood is drained from the appropriate vein embalming fluid, such as formeldahyde or the like, will be inputted through the chosen artery. Typical veins for draining blood include the juggler, femoral and axillary veins. Typically the carotid and femoral arteries are appropriate for introducing the embalming fluid.

The usual procedure is for the vein or artery to be properly exposed by surgical techniques, and for a suitable orifice to be opened in the vein or artery, usually be a scalpel or other surgical device. In actuality, the scalpel is extremely clumsy and generally results in the cutting of an orifice or hole which is of an irregular size or shape. An additional problem is that veins or arteries may break with the use of a scalpel or other prior art device. Breakage of veins or arteries in this manner is particularly common where the deceased had been afflicted with arteriosclerosis. Difficulties are also experienced in preparing smaller sized bodies (such as infants etc.) for embalming because of the very small physical dimensions of the internal arteries and veins.

Besides its inherent clumsiness, the scalpel is also disadvantageous in that it typically requires the simultaneous use of accessory mechanisms. For example, the mortician usually must concurrently operate some form of manipulation device, such as an aneurism needle, to properly position the artery or vein for subsequent penetration by the scalpel. Usually this requires use of both hands, and the entire procedure is clumsy, time consuming and inefficient. The latter circumstances are particularly disadvantageous since the entire embalming process should be performed with minimum scarring or disfigurement of the deceased.

The closest prior art known to me relates to a clamp for blood vessels shown in U.S. Pat. No. 4,106,508. Less relevant prior art is set forth in U.S. Pat. Nos. 3,927,660 and 3,916,875.

SUMMARY OF THE INVENTION

The present invention comprises a manually operable device adapted to puncture blood vessels such as veins or arteries. The device is ideally suited for use in the funeral industry, and its function is primarily to open an appropriately sized and dimensioned orifice in a vein or artery prior to the embalming process.

In the preferred embodiment the invention comprises a handle adapted to be manually closed by the operator to compressively shut associated jaws. Needle means associated with one of the jaw members contacts the vein or artery and opens an appropriate orifice to facilitate subsequent interconnection with conventional embalming machine hardware. The vein or artery may be manipulated with the aid or a fork member secured to the device which helps replace the aneurism needle which may otherwise be required. Preferably the fork member is pivotally adjustable, and its forwardly projecting teeth include notch members adapted to align the vein or artery. Preferably the jaw is provided with a guide channel for aligning the vein or artery directly below the needle member to facilitate exact placement of the orifice to be cut.

In the preferred embodiment the needle employs a unique beveled configuration of generally triangular characteristics. Additionally, the jaws are normally biased by a spring to an open position. To facilitate use of the device with infants and others with reduced physical dimensions, the fork member teeth preferably converge toward each other.

Thus a basic object of the present invention is to provide a manual device for perforating veins or arteries to aid in the embalming process.

A similar object of the present invention is to provide a vein or artery perforating device which will minimize scars or other disfigurement.

Yet another related object is to provide a perforator device of the character described which will replace the scalpel hitherto required for vein or artery preparation.

Another object of the present invention is to provide a perforating device of the character described suitable for locating a low risk penetration point.

A similar object of this invention is to avoid damaging the lumen of the vein or artery during the embalming process.

Yet another object of the present invention is to help minimize the blood clotting which may result unless veins are properly punctured prior to embalming.

These and other objects and advantages of the present invention, along with features of novelty appurtenant thereto, will appear or become apparent in the course of the following descriptive sections.

BRIEF DESCRIPTION OF THE DRAWINGS

In the following drawings, which form a part of the specification and which are to be construed in conjunction therewith, and in which like reference numerals have been employed throughout to indicate like parts in the various views:

FIG. 1 is an isometric view of a preferred embodiment of the present invention illustrating a portion of a vein or artery inserted within its jaws prior to puncturing;

FIG. 2 is a side elevational view of the device of FIG. 1;

FIG. 3 is a top plan view thereof;

FIG. 4 is a side elevational view similar to FIG. 2, but illustrating the jaws of the device in a closed perforating position;

FIG. 5 is an enlarged view of the preferred needle, taken generally along 5—5 of FIG. 2, with parts thereof broken away for clarity;

FIG. 6 is an enlarged, isometric view of the needle cutting point;

DETAILED DESCRIPTION OF THE DRAWINGS

Figure 7:
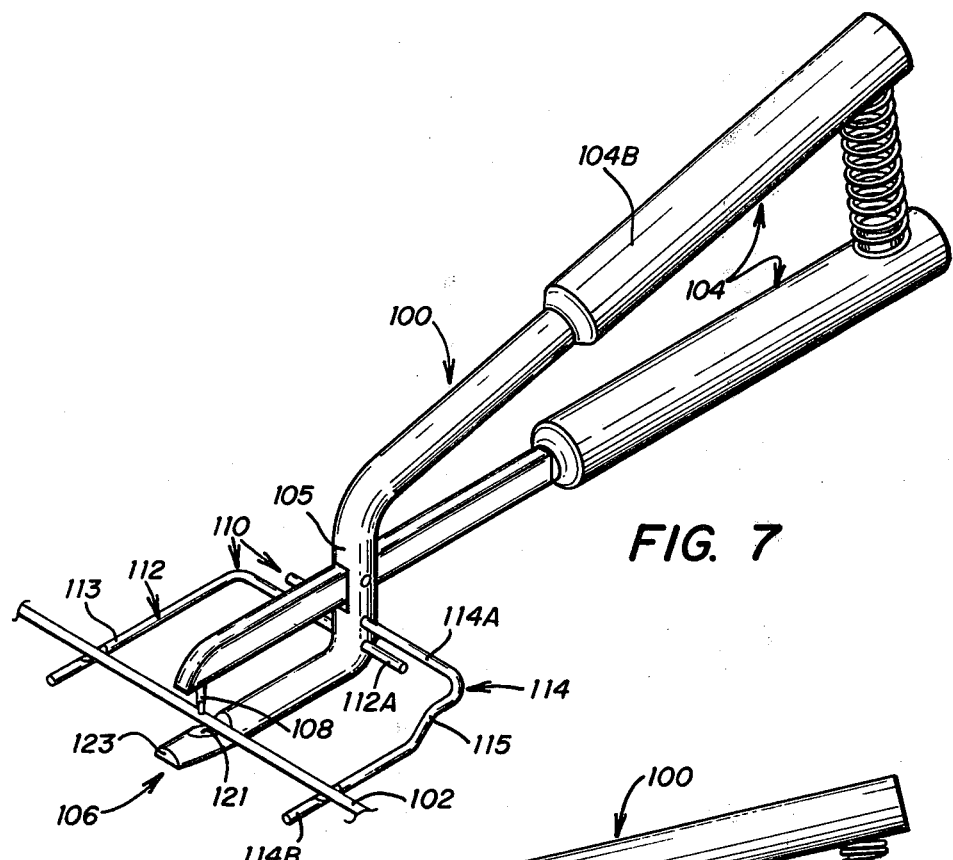
FIG. 7 is an isometric view of an alternative embodiment of the present invention in which different fork construction is employed.

With reference now to the appended drawings, a manual device for perforating a blood vessel is generally designated by the reference numeral 10. Apparatus 10 includes a handle, generally designated by the reference numeral 12, which compressively operates associated jaws, generally designated by the reference numeral 14. As jaws 14 are closed, needle 16 will puncture a vein or artery 18 which is to be perforated prior to the embalming process. A fork, generally designated by the reference numeral 20, is preferably pivotally coupled at the front of the apparatus to aid in the manipulation and subsequent alignment of the vein or artery 18.

Handle 12 is formed from a first elongated, preferably rigid member 22 which includes an offset forwardly projecting front portion 24 and an integral rear portion generally designated by the reference numeral 26. The rear portion may be provided with an optional, generally tubular grip 28 formed of plastic, rubber or the like. The second elongated handle member 30 is generally straight, and it is received through a suitable orifice defined in the generally vertical portion 51 of first handle member 22, being secured for pivotal displacement with respect thereto with a conventional pin 34. The forwardly projecting portion 38 of handle member 30 mounts needle 16. The rear portion 39 of handle member 30 may be provided with a tubular grip 41 similar to grip 28 previously discussed.

As best observed in FIG. 4, compression of the handle will force member 41 towards member 28 against predetermined tension from spring 44. Spring 44 is preferably included to normally maintain the jaws 14 in an open position.

The fork means 20 preferably includes a generally transversely oriented portion 50 received pivotally through generally vertical segment 51 of handle member 22. Fork 20 is thus pivoted with respect to the apparatus, and its forwardly projecting fingers 54, 56 preferably converge towards the front 57 of the device. In this manner manipulation of the vein or artery 18 to be punctured is facilitated, and penetration through incisions of reduced dimensions is enabled.

Prior alignment of the vein or artery 18 is encouraged by an arcuate groove or channel 60, preferably formed opposite needle 16 in the forward portion 24 of handle member 22. As the vein or artery 18 is received and located within channel 60, the needle 16 will be appropriately positioned thereabove, whereby subsequent compression of handle 12 will force needle 16 into a proper cutting alignment wherein its lower leading edge 66 (FIG. 6) will first contact the vein or artery 18. Alignment of the vein or artery 18 is further facilitated by a pair of notches 70, 71 which similarly position or align the vein or artery 18. Thus, by way of example, where the fork means 20 is positioned substantially horizontally with respect to jaw portion 24, the notches 70, 71 will substantially align with groove 60. However, depending upon the circumstances of actual use, the jaw means may be pivoted to assume a required position. For example, the position indicated in dashed lines in FIG. 4 may be desireable.

With reference now to FIGS. 5 and 6, needle 16 preferably includes a lowermost surface 80 of generally triangular configuration. Surface 80 results from confluence of tapered edges 81, 82, and 83. Leading edge 66 forming the bottom of taper 82 and a side of triangular projection 80 forms the initial cutting edge. Hereinafter the aforementioned geometry will be referred to as "triangular". It has been found through experimentation that the geometry discussed works extremely successfully.

It will thus be apparent that the device 10 may be easily handled with one hand of the mortician merely be grasping handle 12. As grips 28, 41 are compressed against yieldable tension from spring 44, the jaws 14 will close, driving forwardly projecting front members 24 and 38 together. As this occurs needle 16 will be driven against the vein or artery 18 nested within channel 60. After penetration of the vein or artery, manual release of handle portion 30 will result in the gradual withdrawal of needle 16 as spring 44 expands. The apparatus may then be withdrawn from contact with vein or artery 18, and the fork 20 may be conveniently pivoted, if necessary, to provide for unobstructed withdrawal.

Figure 8:
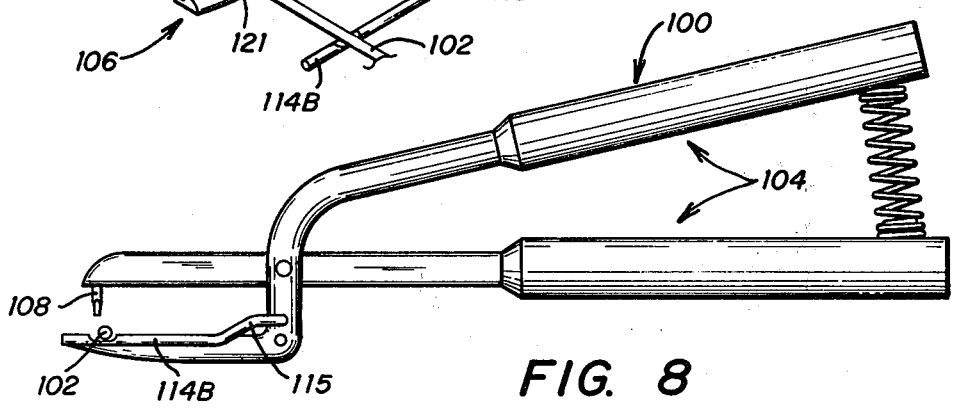
FIG. 8 is a side elevational view of the alternative embodiment of FIG. 7.
Figure 9:
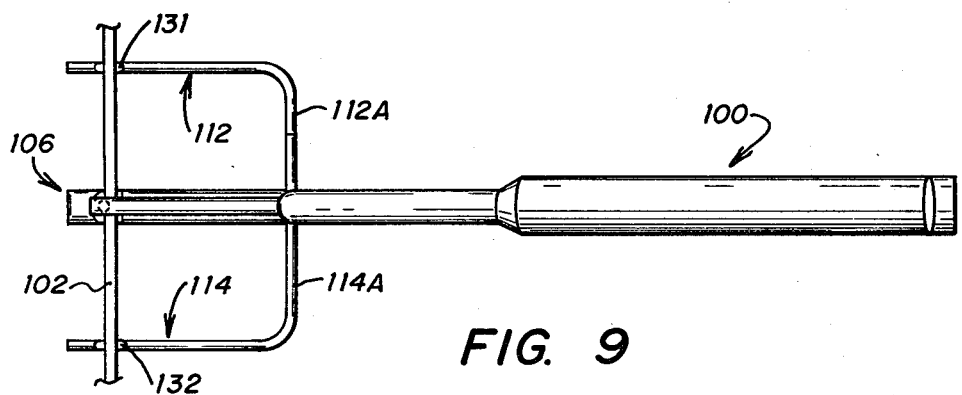
FIG. 9 is a top plan view of said alternative embodiment.

With reference now to FIGS. 7-9, an alternative embodiment 100 is depicted. The perforator 100 operates in substantially the same fashion as embodiment 10 to properly cut a vein or artery 102 for subsequent embalming. When handle 104 is manually compressed by the operator, the front jaws, generally designated by the reference numeral 106, close. It will be apparent that if jaws 106 close, needle 108 will puncture the vein 102 in the manner previously described.

Alternative fork means, generally designated by the reference numeral 110, includes a pair of generally L-shaped members, 112 and 114. Member 112 includes a transverse portion 112A pivotally received through vertical portion 105 of handle member 104B and an integral forwardly projecting member 113 extending towards vein or artery 102. L-shaped member 114 comprises a transverse portion 114A and an integral, forwardly projecting portion 114B. The forward portion 114B is substantially coplanar with L-member portion 113; since L-member 114 is pivotally secured above member 112, arc 115 is warranted.

Fork portions 112 and 114 are thus separately pivotally mounted with respect to the apparatus, and member 114 may thus be adjusted independently of member 112. As in the case of the previously discussed embodiment, a main channel 121 is formed in jaw portion 123 to receive and locate the vein or artery 102 to be punctured. Similarly, notches 131, 132 are provided in the alternative fork construction 110 to facilitate artery or vein manipulation. It will also be appreciated that forks 112, 114 may tend to converge at the front of the apparatus, as in the case of embodiment 10, previously discussed.

The entire vein or artery perforation process may be performed with a minimum of scarring or damage to the deceased. In particular, it should be understood that the device may be constructed in a variety of dimensions, to facilitate successful implementation in conjunction with varying physical dimensions of the deceased. Moreover, it should be understood that the convergent profile of the fork fingers 54, 56 is merely preferred, but that a variety of fork configurations may be employed depending upon circumstances of actual use.

From the foregoing, it will be seen that this invention is one well adapted to obtain all the ends and objects herein set forth, together with other advantages which are obvious and which are inherent to the structure.

It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

What is claimed is:

1. Apparatus for perforating tubular conduit members, said apparatus comprising:
   handle means adapted to be grasped manually by a user of said apparatus;
   jaw means adapted to close in response to compression of said handle means;
   needle means associated with said jaw means for puncturing a tubular conduit member when said jaw means closes
   said jaw means including groove means for properly positioning said tubular conduit member with respect to said needle means; and,
   fork means pivotally secured relative to said jaw means to facilitate manipulation of said tubular conduit member.

2. The combination as defined in claim 1 wherein said fork means includes notch means for assisting in correct positioning of said tubular conduit means prior to puncturing.

3. The combination as defined in claim 2 wherein said needle means terminates in a generally triangular point.

4. The combination as defined in claim 2 including spring means for normally maintaining said jaw means in an open position.

5. Apparatus for perforating tubular conduit members, said apparatus comprising:
   handle means adapted to be grasped manually by a user of said apparatus;
   jaw means adapted to close in response to compression of said handle means;
   needle means associated with said jaw means for puncturing a tubular conduit member when said jaw means closes;
   said jaw means including groove means for properly positioning said tubular conduit member with respect to said needle means; and,
   fork means associated with said jaw means to facilitate manipulation of said tubular conduit member, said fork means comprising separate L members each pivotally secured relative to said jaw means.

6. The combination as defined in claim 5 wherein each of said fork L-members include notch means for assisting and correct positioning of said tubular conduit means prior to puncturing.

7. A device for puncturing a vein or artery, said device comprising:
   a first generally rigid, elongated handle member having a rear portion and a forwardly projecting front portion;
   a second generally rigid, elongated handle member pivotally coupled to said first member and having a rear portion and a forwardly projecting front portion;
   the rear portion of said first and second handle means adapted to be grasped manually and compressed together whereby to urge the forwardly projecting front portion of said second handle member and said forwardly projecting portion of said first handle member together;
   needle means associated with said second handle member front portion for puncturing a vein or artery;
   fork means pivotally coupled to said device for properly positioning a vein or artery to be punctured relative to said needle means.

8. The combination as defined in claim 7 including groove means formed in said forwardly projecting portion of said first handle member for receiving and aligning said vein or artery for correct penetration by said needle means, in cooperation with said fork means.

9. The combination as defined in claim 8 wherein said fork means includes notch means adapted to align and properly position said vein or artery for puncture by said needle means in cooperation with said groove means.

10. The combination as defined in claim 1 wherein said needle means terminates in a triangular point.

11. The combination as defined in claim 7 wherein said fork means comprises:
    a first generally transversely oriented portion; and,
    first and second forwardly projecting teeth members for facilitating manipulation and positioning of a vein or artery to be punctured.

12. The combination as defined in claim 11 wherein said fork means transversely oriented portion is pivotally secured through said first handle member front portion.

13. The combination as defined in claim 12 wherein said first and second teeth members converge toward each other.

14. The combination as defined in claim 13 wherein said needle means terminates in a triangular point.

15. The combination as defined in claim 14 wherein said fork means forwardly projecting teeth include notch means adapted to properly position said vein or artery.

16. The combination as defined in claim 15 wherein said first and second teeth members converge toward each other.

17. A device for puncturing a vein or artery, said device comprising:
    a first generally rigid, elongated handle member having a rear portion and a forwardly projecting front portion
    a second generally rigid, elongated handle member pivotally coupled to said first member and having a rear portion and a forwardly projecting front portion;
    the rear portions of said first and second handle means adapted to be grasped manually and compressed together whereby to urge the forwardly projecting front portion of said second handle member and said forwardly projecting portion of said handle member together;
    needle means associated with said second handle member front portion for puncturing a vein or artery;
    fork means pivotally coupled to said device for aiding in manipulation and positioning of a vein or artery to be punctured; said fork means comprising:
    a first generally transversely oriented portion; and,
    first and second forwardly projecting generally converging teeth members for facilitating manipulation and positioning of a vein or artery to be punctured, said teeth members including notch means adapted to aid in properly positioning said vein or artery.

18. The combination as defined in claim 17 wherein said means for properly positioning said vein or artery to be punctured comprises groove means formed in said forwardly projecting portion of said first handle member for receiving and aligning said vein or artery for correct penetration by said needle means.

19. A device for puncturing a vein or artery, said device comprising:
- a first generally rigid, elongated handle member having a rear portion and a forwardly projecting front portion
- a second generally rigid, elongated handle member pivotally coupled to said first member and having a rear portion and a forwardly projecting front portion;
- the rear portions of said first and second handle means adapted to be grasped manually and compressed together whereby to urge the forwardly projecting front portion of said second handle member and said forwardly projecting portion of said first handle member together;
- needle means associated with said second handle member front portion for puncturing a vein or artery; and,
- fork means associated with said device for aiding in the manipulation and alignment of a vein or artery prior to its puncture, said fork means comprising:
  - a first generally transversely oriented portion pivotally coupled to said device; and,
  - first and second forwardly projecting notched teeth members for aiding in manipulating a vein or artery.

20. The combination as defined in claim 19 wherein said needle means terminates in a triangular point.

21. The combination as defined in claim 20 wherein said first and second teeth members converge each other.

22. A device for puncturing a vein or artery, said device comprising:
- a first generally rigid, elongated handle member having a rear portion and a forwardly projecting front portion
- a second generally rigid, elongated handle member pivotally coupled to said first member and having a rear portion and a forwardly projecting front portion;
- the rear portions of said first and second handle means adapted to be grasped manually and compressed together whereby to urge the forwardly projecting front portion of said second handle member and said forwardly projecting portion of said first handle member together;
- needle means associated with said second handle member front portion for puncturing a vein or artery; and
- fork means associated with said device for aiding in the proper positioning of a vein or artery to be punctured relative to said needle means; said fork means comprising a pair of cooperating L-members, each L member seperately pivotally coupled to said device.

23. The combination as defined in claim 22 wherein each of said L-members includes notch means adapted to align and properly position said vein or artery for puncture by said needle means.

24. The combination as defined in claim 23 wherein said means for properly positioning said vein or artery to be punctured comprises groove means formed in said forwardly projecting portion of said first handle member for receiving and aligning said vein or artery for correct penetration by said needle means.

* * * * *